United States Patent

Buijs et al.

[19]

[11] Patent Number: 6,011,153

[45] Date of Patent: Jan. 4, 2000

[54] PROCESS FOR THE PREPARATION OF A MIXTURE OF ε-CAPROLACTAM, 6-AMINOCAPROIC ACID AND 6-AMINOCAPROIC AMIDE

[75] Inventors: Wim Buijs, Schinnen; Henricus F. W. Wolters, Echt, both of Netherlands

[73] Assignees: DSM N.V., Heerlen, Netherlands; EI du Pont de Nemours and Company, Wilmington, Del.

[21] Appl. No.: 09/140,896

[22] Filed: Aug. 21, 1998

Related U.S. Application Data

[63] Continuation of application No. PCT/NL97/00057, Feb. 12, 1997.

[30] Foreign Application Priority Data

Feb. 23, 1996 [NL] Netherlands ............................ 1002429

[51] Int. Cl.$^7$ ...................... C07D 201/12; C07D 201/02; C07D 201/08
[52] U.S. Cl. ............................................. 540/533; 540/538
[58] Field of Search ...................................... 540/533, 538

[56] References Cited

U.S. PATENT DOCUMENTS 3,485,821  12/1969  Sheehan et al. ...................... 260/239.3
4,599,199  7/1986   Fuchs et al. .......................... 260/239.3
4,730,040  3/1988   Vagt et al. ............................... 540/538
5,395,974  3/1995   McKinney ............................... 564/488

OTHER PUBLICATIONS

Abstract JP 47010715, Mar. 30, 1972.

*Primary Examiner*—Mukund J. Shah
*Assistant Examiner*—Bruck Kifle
*Attorney, Agent, or Firm*—Pillsbury, Madison & Sutro, LLP

[57] ABSTRACT

Process for the preparation of a mixture of ε-caprolactam, 6-aminocaproic acid and 6-aminocaproic amide by heating an aqueous mixture containing ammonia and oligomers of 6-aminocaproic acid and/or of 6-aminocaproic amide, the aqueous mixture containing 0.5–7 wt. % of equivalent ammonia (calculated as $NH_3$) and the temperature lying between 280° C. and 330° C., in which by "equivalent ammonia" is meant free ammonia and ammonia present in the form of a terminal amide group of one of the compounds present in the aqueous mixture.

6 Claims, No Drawings

PROCESS FOR THE PREPARATION OF A MIXTURE OF ε-CAPROLACTAM, 6-AMINOCAPROIC ACID AND 6-AMINOCAPROIC AMIDE

This is a Continuation of: International Appln. No. PCT/NL97/00057 filed Feb. 12,1997 which designated the U.S.

The invention relates to a process for the preparation of a mixture of ε-caprolactam, 6-aminocaproic acid and 6-aminocaproic amide by heating an aqueous mixture containing ammonia and oligomers of 6-aminocaproic acid and/or of 6-aminocaproic amide.

JP-B-72010715 describes a process for the preparation of ε-caprolactam by heating 6-aminocaproic acid and/or 6-aminocaproic amide in water in the presence of 5–30 wt. % ammonia at a temperature between 200° C. and 380° C. After the reaction ε-caprolactam is isolated from the reaction mixture through extraction or distillation. After the isolation of the ε-caprolactam, the extraction or distillation residue still contains unreacted 6-aminocaproic acid and/or 6-aminocaproic amide and oligomers of these two compounds. These oligomers of 6-aminocaproic acid and/or 6-aminocaproic amide are formed during the cyclisation reaction of 6-aminocaproic acid and/or 6-aminocaproic amide. For example, Example 1 of JP-B-72010715 discloses a process that results in a high yield of ε-caprolactam at 380° C. in combination with an ammonia concentration of 28 wt. %. This high yield is achieved when the aforementioned aqueous extraction or distillation residue, containing the oligomers of 6-aminocaproic acid and/or 6-aminocaproic amide, is recirculated to the reactor.

A drawback of this known process is that the total yield of ε-caprolactam, 6-aminocaproic acid and 6-aminocaproic amide relative to the oligomer substrate of the latter two compounds is low. In a process for the preparation of ε-caprolactam, the compounds 6-aminocaproic acid and 6-aminocaproic amide are not undesired products, because—as is known—these compounds can be converted into ε-caprolactam with a high yield. These compounds are also known as ε-caprolactam precursors. A further drawback of this known process is that it has been found that the quality of the ε-caprolactam ultimately obtained is relatively poor, probably because small amounts of byproducts are formed in this process. It is difficult, if not impossible, to remove these byproducts from the ε-caprolactam product stream. As a result, the ultimate product cannot be used on an industrial scale as a raw material for Nylon-6.

The object of the invention is a process according to which the oligomers described above can be converted into ε-caprolactam, 6-aminocaproic acid and 6-aminocaproic amide with a high yield.

This object is achieved with the process according to the invention because the aqueous mixture contains 0.5–7 wt. % of equivalent ammonia (calculated as $NH_3$) and the temperature lies between 280° C. and 330° C., in which by "equivalent ammonia" is meant free ammonia and ammonia present in the form of a terminal amide group of one of the compounds present in the aqueous mixture.

It has been found that with the process according to the invention the amount of byproducts in the ε-caprolactam product stream is considerably and signifcantly smaller than that which is obtained with the process according to the state of the art.

An advantage of the process according to the invention is that a high yield of ε-caprolactam and ε-caprolactam precursors can be obtained. Another advantage of the process according to the invention is that ε-caprolactam with high purity can be obtained. A further advantage of the process according to the invention is that the ε-caprolactam fraction in the overall amount of ε-caprolactam and ε-caprolactam precursors is relatively high. When the higher ammonia concentrations of JP-B-72010715 are used at 280° C.–330° C., a significantly lower fraction of ε-caprolactam is obtained. A high fraction of ε-caprolactam presents the advantage that a smaller amount of ε-caprolactam precursors has to be converted into ε-caprolactam in subsequent steps. This means that process equipment of a smaller scale can be used.

U.S. Pat. No. 3,485,821 describes a process for the preparation of ε-caprolactam in which 6-aminocaproic acid is cyclised in an aqueous 1 wt. % ammonia solution at a temperature of 260° C. in the absence of oligomers. U.S. Pat. No. 3,485,821 further discloses that higher yields of ε-caprolactam can be obtained at the same temperature (260° C.) if no ammonia is present. However, this patent does not describe the reaction of oligomers of 6-aminocaproic acid into ε-caprolactam and 6-aminocaproic acid in the presence of (equivalent) ammonia.

U.S. Pat. No. 4,730,040 describes that a cyclisation reaction of 6-aminocaproic acid must be carried out in water in the absence of ammonia because otherwise the yield of ε-caprolactam is adversely affected. This patent does hence not describe the reaction of oligomers of 6-aminocaproic acid in the presence of ammonia into ε-caprolactam and 6-aminocaproic acid.

Suitable oligomers according to the present invention are a mixture of linear oligomers of 6-aminocaproic acid, linear oligomers of 6-aminocaproic amide and/or cyclic oligomers of same. The linear oligomers of 6-aminocaproic acid can be represented by the general formula $H[NH(CH_2)_5CO]_nOH$, where n generally corresponds to a number between 2 and 10 inclusive. The linear oligomers of 6-aminocaproic amide can be represented by the general formula $H[NH(CH_2)_5CO]_nNH_2$, where n generally corresponds to a number between 2 and 10, inclusive. Most oligomers are dimers and trimers.

The amount of oligomers in the aqueous mixture generally exceeds 1 wt. %. The amount of oligomers is generally less than 20 wt. %, preferably less than 10 wt. % and most preferably less than 7 wt. %.

Ammonia may be added to the aqueous mixture or it may already be present in a reaction mixture, which also contains oligomers of 6-aminocaproic acid and/or 6-aminocaproic amide, obtained in a previous process step.

The amount of (equivalent) ammonia in the aqueous mixture according to the invention is between 0.5 and 7 wt. % of equivalent ammonia (calculated as $NH_3$). The term "equivalent ammonia" means free ammonia and ammonia present in the form of a terminal amide group of one of the compounds present in the aqueous mixture. The compound containing a terminal amide group is generally for the greater part 6-aminocaproic amide. Other compounds containing a terminal amide group, are oligomers of 6-aminocaproic amide, for example $H_2N(CH_2)_5C(O)NH(CH_2)_5C(O)NH_2$ (dimer) and $H_2N(CH_2)_5C(O)NH(CH_2)_5C(O)NH(CH_2)_5C(O)NH_2$ (trimer). The molar amount of equivalent ammonia is generally the sum of the molar amount of free ammonia and generally the molar amount of compounds containing one terminal amide group. For example one mol of a dimer of 6-aminocaproic amide equals one mol equivalent ammonia. One mol of a compound containing two terminal amide groups represents two moles equivalent ammonia. The wt. % of equivalent ammonia can now be calculated starting from the molar amount of equivalent ammonia using the molecular weight of $NH_3$.

Because of the presence of equivalent ammonia the amount of ε-caprolactam and the ε-caprolactam precursors in the reaction mixture appears to increase. The amount of equivalent ammonia is preferably chosen to be as low as possible. This is because it has been found that the fraction of ε-caprolactam in the total amount of ε-caprolactam and ε-caprolactam precursors, i.e. 6-aminocaproic acid and/or 6-aminocaproic amide decreases as the equivalent ammonia concentration increases. The equivalent ammonia concentration is preferably chosen to be lower than 3 wt. %.

The equivalent ammonia concentration can also be kept at and/or brought to the desired value within the above general and preferred ranges by adding ammonia or by removing ammonia, for example by stripping.

A preferred embodiment of the process according to the invention is a process in which the equivalent ammonia is present as 6-aminocaproic amide, This is advantageous because it is then not necessary to add free ammonia separately.

Without limiting ourselves to the following theory, we expect that a large portion of the free ammonia is bound as amide compounds and that the increased presence of these compounds, such as 6-aminocaproic amide, and of any residual free $NH_3$ is responsible for the favourable effect according to the invention. It has been found that the favourable effect according to the invention is achieved with the presence of between 5 and 40 wt. % 6-aminocaproic amide. Most preferably, the 6-aminocaproic amide concentration of the aqueous mixture is between 8 and 20 wt. %.

In the process according to the invention 6-aminocaproic acid may also be added to the aqueous mixture. The concentration of 6-aminocaproic acid in the aqueous mixture is preferably between 2 and 15 wt. %.

In the process according to the invention ε-caprolactam may also be added to the aqueous mixture. The concentration of the ε-caprolactam in the aqueous mixture is preferably between 0.1 and 20 wt. %.

The process according to the invention can be applied with particular advantage using an aqueous mixture obtained in a previous process step, which mixture already contains oligomers of 6-aminocaproic amide and/or 6-aminocaproic acid, preferably also 6-aminocaproic amide, and optionally 6-aminocaproic acid and/or ε-caprolactam. The aqueous mixture containing the above oligomers, ε-caprolactam, 6-aminocaproic acid and/or 6-aminocaproic amide can for example be obtained through reductive amination of 5-formylvaleric acid or its ester.

The concentration of the above oligomers and 6-aminocaproic amide and optionally 6-aminocaproic acid and/or ε-caprolactam is preferably between 10 and 40 wt. %. Most preferably this concentration is higher than 15 wt. %. These high concentrations are advantageous in a commercial process because then process equipment of a smaller scale is needed, which results in lower investment costs.

The pressure of the cyclisation generally should be the same as or higher than the equilibrium pressure of the liquid reaction mixture at the applied temperature. The pressure should be such that the reaction mixture in the process according to the invention is obtained as a liquid.

The cyclisation can be carried out batchwise or in a continuous process.

In a commercial process the reaction is preferably carried out in continuous mode in a suitable reactor. Examples of suitable reactors are tube reactors, continuously mixed reactors or several mixed reactors in series.

After the reaction, in which a reaction mixture rich in ε-caprolactam is obtained, the ε-caprolactam can be recovered using any separation technique known to a person skilled in the art. Examples of suitable separation techniques are crystallisation, (vacuum) distillation and extraction. Preferably, ε-caprolactam is separated by extraction using an organic extraction agent. Examples of suitable organic extraction agents are methylene chloride, cyclohexane, chloroform, toluene, benzene, tetrachloroethane and trichloroethene. Preferred extraction agents are (cyclic) aliphatic organic compounds having one or more hydroxy groups which are liquid under the extraction conditions and substantially immiscible with water. Such (poly) alcohols have preferably 5–12 carbon atoms. These extraction agents are preferred because they have a better extraction efficiency than the chlorinated organic compounds as described above. These extraction agents are furthermore preferred because their use does not result in any environmental objections. Preferably one or two and more preferably only one hydroxy group is present. Examples of compounds having two hydroxy groups are hexanediol, nonanediol, neopentylglycol, methyl-methylpropanediol, ethyl-methylpropanediol or butyl-methylpropanediol. Examples of compounds having one hydroxy group are cyclohexanol, 4-methyl-2-pentanol, 2-ethyl-1-hexanol, 2-propyl-1-heptanol, n-octanol, iso-nonylalcohol, n-decylalcohol and mixtures of linear and branched $C_8$-alcohols, mixtures of linear and branched $C_9$-alcohols and mixtures of linear and branched $C_{10}$-alcohols. Mixtures of the above mentioned alcohols can also be used.

If ε-caprolactam is recovered through distillation, it is preferable that not all of the ε-caprolactam is separated from the reaction mixture. It has been found that if the distillation residue contains a small amount of ε-caprolactam, the oligomers of 6-aminocaproic acid and/or 6-aminocaproic amide will less easily solidify. The distillation residue preferably contains between 5 and 50 wt. % ε-caprolactam.

The distillation residue from the reaction mixture, containing a small amount of ε-caprolactam, will usually also contain non-converted oligomers, 6-aminocaproic acid and 6-aminocaproic amide.

The process according to the invention can be used with particular advantage in a process for the preparation of ε-caprolactam in which ε-caprolactam is separated from the aqueous reaction mixture, and in which the thus obtained ε-caprolactam-poor mixture which mixture contains at least an amount of non-converted oligomers, 6-aminocaproic acid and 6-aminocaproic amide, is reused in the process according to the invention. It has been found that if this recirculation is applied, the process according to the invention can be carried out so as to result in a significantly high yield of ε-caprolactam of almost 100%.

This embodiment of the invention is preferably carried out in continuous mode.

The invention will be further elucidated by means of the non-limiting examples given below.

The following abbreviations will be used: 6-ACA=6-aminocaproic acid, 6-ACAM=6-aminocaproic amide and CAP=ε-caprolactam. 'Mol oligomers' is understood to be the equivalent ε-caprolactam concentration in mol, which can hypothetically be formed by that amount of oligomers.

In the examples the monomer yield (mol. %) is calculated as follows: the total of the amounts (in mol) of 6-ACA, 6-ACAM and CAP present in the mixture that leaves the reactor is divided by the total of the amounts (in mol) of 6-ACA, 6-ACAM, CAP and oligomers present in the mixture that is fed to the reactor. This figure is then multiplied by 100%.

In the examples the ε-caprolactam yield (mol. %) is calculated as follows: the amount (in mol) of ε-caprolactam present in the mixture that leaves the reactor is divided by the total of the amounts (in mol) of 6-ACA, 6-ACAM, CAP and oligomers present in the mixture that is fed to the reactor. This figure is then multiplied by 100%.

The aqueous mixture and the resulting reaction mixture were analysed using, among other techniques, HPLC (high-pressure liquid chromatography), GLC (gas liquid chromatography), GPC (gel permeation chromatography) and NMR (nuclear magnetic resonance).

EXAMPLE I

An aqueous mixture containing 0.03 wt. % 6-aminocaproic acid, 0.39 wt. % ε-caprolactam, 0.5 wt. % oligomers and 6 wt. % $NH_3$ was fed to a cyclisation reactor. The cyclisation reactor was a continuously mixed reactor with a volume of 2 l. The reactor's temperature was kept at a constant value of 290° C. with the aid of an oil bath. The pressure was 10 MPa. After a residence time of 60 min. the monomer yield (one passage) was 95.8 mol. % and the ε-caprolactam yield was 77.1 mol. %.

Comparative Experiment A

Example I was repeated, only now the aqueous mixture contained 0 wt. % $NH_3$. The monomer yield was 91.0 mol. % and the ε-caprolactam yield was 83.6 mol. %

EXAMPLE II

An aqueous mixture containing 22.1 wt. % organic components, which 22.1 wt. % comprises: 14.2 mol. % 6-aminocaproic acid, 39.9 mol. % 6-aminocaproic amide, 33.9 mol. % ε-caprolactam and 12.0 mol. % oligomers, was fed in continuous mode to a cyclisation reactor at a flow rate of 742 g/hour (1.33 mol/hour of the aforementioned compounds). 85 g/hour (about 0.715 mol/hour) of a distillation residue (see below) and 314 g/hour $H_2O$ were also fed to the cyclisation reactor. So a total of 1141 g/hour of product mixture (21.8 wt. % products) was fed to the cyclisation reactor (249 g/hour ε-caprolactam, ε-caprolactam precursors and oligomers and 892 g/hour $H_2O$).

The cyclisation was carried out in a tube reactor at a constant temperature of 300° C. (with the aid of an oil bath), a pressure of 10 MPa and a residence time of about 30 min.

After cooling and reduction of the pressure the effluent of the cyclisation reactor was analysed. The mixture contained 0.5 mol. % ε-caprolactam, 10.8 mol. % 6-ACA(M) and 18.7 mol. % oligomers.

The cyclisation effluent mixture was fed, in continuous mode, to 2 vacuum distillation columns placed in series. In the first column the solvent ($H_2O$) was removed. In the second column ε-caprolactam was isolated at a rate of 150 g/hour (1.33 mol/hour).

The distillation residue obtained as the bottom flow in the second distillation column (containing about 0.715 mol/hour ε-caprolactam, ε-caprolactam precursors and oligomers) was recirculated in continuous mode to the cyclisation reactor (see above) at a rate of 85 g/hour.

So a 100% yield of ε-caprolactam could be obtained by recirculating the distillation residue after a portion of the ε-caprolactam had been removed.

The above results were obtained 3 hours after the continuous process had stabilised.

We claim:

1. Process for the preparation of a mixture of ε-caprolactam, 6-aminocaproic acid and 6-aminocaproic amide by heating an aqueous mixture containing ammonia, 6-aminocaproic amide and lineair and/or cyclic oligomers of 6-aminocaproic acid and/or of 6-aminocaproic amide and optionally 6-aminocaproic acid and/or ε-caprolactam, characterised in that the aqueous mixture contains 0.5–7 wt. % of equivalent ammonia (calculated as $NH_3$), 1–20 wt. % of the oligomers, 5–40 wt. % 6-aminocaproic amide, that the concentration of the oligomers and 6-aminocaproic amide and optionally 6-aminocaproic acid and/or ε-caprolactam in the aqueous mixture is between 10 and 40 wt. % and that the temperature is between 280° C. and 330° C., in which by "equivalent ammonia" is meant free ammonia and ammonia present in the form of a terminal amide group of one of the compounds present in the aqueous mixture.

2. Process according to claim 1, characterised in that the aqueous mixture contains less than 3 wt. % of equivalent ammonia.

3. Process according to claim 2, characterised in that the aqueous mixture contains between 8 and 20 wt. % 6-aminocaproic amide.

4. Process for the preparation of ε-caprolactam, according to which ε-caprolactam is separated from the aqueous reaction mixture obtained according to the process according to any one of claims 1–3 and according to which the thus obtained ε-caprolactam-poor mixture, which mixture contains at least an amount of non-converted oligomers, 6-aminocaproic acid and 6-aminocaproic amide, is reused in the process according to any one of claims 1–3.

5. Process according to claim 4, characterized in that the separation of ε-caprolactam is performed by extraction using an organic extraction agent.

6. Process according to claim 5, characterized in that the extraction agent is a (poly)alcohol having 5–12 carbon atoms.

* * * * *